US011751818B2

(12) United States Patent
Schneider (10) Patent No.: US 11,751,818 B2
(45) Date of Patent: Sep. 12, 2023

(54) METHOD AND SYSTEM FOR CREATING A ROADMAP FOR A MEDICAL WORKFLOW

(71) Applicant: Siemens Healthcare GmbH, Erlangen (DE)

(72) Inventor: Rainer Schneider, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 349 days.

(21) Appl. No.: 17/031,864

(22) Filed: Sep. 24, 2020

(65) Prior Publication Data

US 2021/0085260 A1 Mar. 25, 2021

(30) Foreign Application Priority Data

Sep. 25, 2019 (EP) .................................... 19199567

(51) Int. Cl.
| | | |
|---|---|---|
| *A61B 5/00* | (2006.01) | |
| *G16H 40/20* | (2018.01) | |
| *G16H 30/20* | (2018.01) | |
| *G16H 50/30* | (2018.01) | |
| *G16H 50/70* | (2018.01) | |

(Continued)

(52) U.S. Cl.
CPC .......... *A61B 5/7289* (2013.01); *A61B 5/0044* (2013.01); *A61B 5/055* (2013.01); *G01R 33/5608* (2013.01); *G01R 33/5676* (2013.01); *G01R 33/56308* (2013.01); *G06T 7/20* (2013.01); *G16H 30/20* (2018.01); *G16H 40/20* (2018.01); *G16H 40/63* (2018.01); *G16H 50/30* (2018.01); *G16H 50/70* (2018.01);

(Continued)

(58) Field of Classification Search
CPC ..... A61B 5/7289; A61B 5/055; A61B 5/0044; G01R 33/5608; G01R 33/56308; G01R 33/5676; G06T 2207/10088; G06T 7/20; G06T 2207/30048; G06T 2207/30061; G16H 30/20; G16H 50/70
See application file for complete search history.

(56) References Cited

U.S. PATENT DOCUMENTS

| | | | |
|---|---|---|---|
| 11,026,636 B2 * | 6/2021 | Speier | .................. A61B 5/1107 |
| 2011/0038520 A1 * | 2/2011 | Yui | ..................... G01R 33/5676 |
| | | | 324/309 |
| 2013/0225943 A1 * | 8/2013 | Holsing | ................... A61B 6/12 |
| | | | 600/409 |

FOREIGN PATENT DOCUMENTS

DE 102015224162 A1 * 11/2017 ............. A61B 5/055

OTHER PUBLICATIONS

Wetzl et al. 2016 Proc. Intl. Soc. Mag. Reson. Med. 24 (2016) Abstract 2016 3 pages with enlarged Figures (Year: 2016).*

(Continued)

*Primary Examiner* — Keith M Raymond
*Assistant Examiner* — Patrick M Mehl
(74) *Attorney, Agent, or Firm* — Lempia Summerfield Katz LLC (57) ABSTRACT

A method for creating a roadmap for a medical workflow includes providing a multidimensional image-dataset including a plurality of images of a predefined organ combined with a number of state-dimensions characterizing a movement state of a moving organ. Measured pilot tone data is provided from a continuous pilot tone signal acquisition. A coordinate is determined for each state-dimension based on the measured pilot tone data, and an image of the multidimensional image-dataset is selected based on the number of determined coordinates of each state dimension.

12 Claims, 4 Drawing Sheets

(51) Int. Cl.
- G16H 40/63 (2018.01)
- A61B 5/055 (2006.01)
- G01R 33/56 (2006.01)
- G01R 33/563 (2006.01)
- G01R 33/567 (2006.01)
- G06T 7/20 (2017.01)

(52) U.S. Cl.
CPC .............. G06T 2207/10088 (2013.01); G06T 2207/30048 (2013.01); G06T 2207/30061 (2013.01)

(56) References Cited

OTHER PUBLICATIONS

Feng et al. 2018 Magnetic Resonance in Medicine 79:826-838; ePub May 11, 2017 (Year: 2018).*

Campbell-Washburn et al. 2017 J. Mag. Reson. Imag. 46:935-950; (Year: 2017).*

Rank (2016 PhD Thesis University of Heidelberg, Germany, 124 pages; (Year: 2016).*

Bacher et al. 2018 Proc. Intl. Soc. Mag. Reson. Med. 26:4913 (Year: 2018).*

Bacher, Mario. "Cardiac triggering based on locally generated pilot-tones in a commercial MRI scanner: a feasibility study." Institute for Medical Engineering—Graz University of Technology (Year: 2017) (2017).

European Search Report for European Application No. 19199567.9—1126 dated Apr. 1, 2020.

Feng, L. I., et al. "5D whole-heart sparse MRI." Magnetic resonance in medicine 79.2 (2018): 826-838.

Schroeder, Lea, et al. "A novel method for contact-free cardiac synchronization using the pilot tone navigator." Proceedings of the 24th Annual Meeting of ISMRM, Singapore. 2016. pp. 1-3.

Xu, Robert, and Graham A. Wright. "GPU accelerated dynamic respiratory motion model correction for MRI-guided cardiac interventions." Computer methods and programs in biomedicine 136 (2016): 31-43.

* cited by examiner

METHOD AND SYSTEM FOR CREATING A ROADMAP FOR A MEDICAL WORKFLOW

This application claims the benefit of European Patent Application No. EP 19199567.9, filed on Sep. 25, 2019, which is hereby incorporated by reference in its entirety.

BACKGROUND

The present embodiments describe a method and a system for the creation of a roadmap for a medical workflow and, more specifically, a roadmap for a medical workflow in the technical field of magnetic resonance imaging (MRI).

MRI-systems are used in medical examinations for recording (e.g., imaging) data of an examination object by exciting nuclear spins that are aligned within a strong basic magnetic field. The precession or relaxation of the spins from this excited state into a state with less energy generates, as a response, a magnetic alternating field ("RF-signal") that is received via RF-antennae. The RF-frequency strongly depends on the basic magnetic field.

Depending on the pulse sequence used for recording, the measurement of the MRI-system requires a number of milliseconds up to seconds. While a longer recording time usually results in minimal noise artifacts, the influence of motion artifacts increases with the duration of the measurement. Although most patients try to remain still, in order to avoid motion artifacts, there are unavoidable movements of the patient that cannot be stopped, such as, for example, breathing or heartbeat.

In addition, during an intervention, there may be the case that the respective organ and a device necessary for the invention may not be seen on the recorded images at the same time due to different contrasts.

The typical EP workflow includes a 3D roadmap that is the central component throughout the whole procedure. More precisely, the roadmap is 3D acquisition of an organ (e.g., the whole heart) that is used to overlay current positions of a device (e.g., an endoscope or a catheter) that is actively tracked relative to the organ (e.g., the heart) to guide the operator by reformatting 2D slices out of the 3D volume according to the current device position and to enable a segmentation of the organ (e.g., the four chambers of a heart) for further post-processing and visualization options. The 3D dataset is acquired once before the whole workflow and is used to plan and guide the procedure.

This roadmap offers only limited accuracy by continuous movement of the heart due to breathing and cardiac cycle. Thus, there is a dynamic mismatch of the tracked device relative to the roadmap, which is, for example, crucial when targeting small lesions of 1 mm size.

Up to now, this issue of a live motion resolved roadmap is currently not addressed, and applications are typically pursued based on the static 3D roadmap with all known limitations.

Early work has been pursued to perform a 2D-3D registration of incoming image data to the roadmap (Xu, Robert, and Graham A. Wright, "GPU accelerated dynamic respiratory motion model correction for MRI-guided cardiac interventions," Computer methods and programs in biomedicine 136 (2016): 31-43). However, potential image registration methods are to be non-rigid and are to be able to address many different contrasts in real-time. Computational efforts and robustness are difficult to obtain.

SUMMARY AND DESCRIPTION

The scope of the present invention is defined solely by the appended claims and is not affected to any degree by the statements within this summary.

The present embodiments may obviate one or more of the drawbacks or limitations in the related art. For example, known systems, devices, and methods are improved, and a solution for the fast creation of a dynamic roadmap for a medical workflow is provided.

This present embodiments provide a solution based on the combination of the pilot tone technique (see, e.g., Schroeder, Lea, et al. "A novel method for contact-free cardiac synchronization using the pilot tone navigator," Proceedings of the 24th Annual Meeting of ISMRM, Singapore, 2016) and high dimensional datasets for providing a live motion resolved roadmap.

A method according to the present embodiments may be used for the creation of a roadmap (e.g., a dynamic roadmap) for a workflow in the technical field of MRI. A roadmap shows the actual state of a region of a patient and may be used to localize a medical device in this region or simply to show this region. The road map typically includes an actual image of the region, where the image does not have to be actually recorded (e.g., at least partly), but nevertheless represents the actual situation in this region.

The method includes the following acts, where the method may be used in the course of an examination of a patient or an intervention to a patient. A multidimensional image-dataset including a plurality of images of a predefined organ combined with a number of state-dimensions characterizing the movement state of a moving organ is provided. Measured pilot tone data is provided from a continuous pilot tone signal acquisition. A coordinate is determined for each state-dimension based on the measured pilot tone data. An image of the multidimensional image-dataset is selected based on the number of determined coordinates of each state dimension.

The selected image may be displayed on a display unit and/or made available in electronic form at an output of a processor (e.g., as a data file).

Regarding the act of providing a multidimensional image-dataset, the multidimensional image-dataset includes a plurality of 2D or 3D images (e.g., reconstructed images). These images may be MR images, but may also be or include other images, such as CT images, ultrasound images, or simulated images. The images in the multidimensional image-dataset are connected with coordinates of a number of further dimensions (e.g., "state-dimensions") that are especially time-like.

These state-dimensions represent the movement states of a moving organ and include definite coordinates (e.g., certain movement states of this moving organ). The movement states may be characterized by points of time, time-intervals, or signal shapes (e.g., of a measured pilot tone signal). It is not necessary that the moving organ is identical or non-identical with the predefined organ. Thus, in the case the predefined organ is the heart, one state-dimension may characterize the movement of the heart itself; however, one other state-dimension may characterize the movement of the lung. In the case the predefined organ is the liver, it is not necessary that the liver has to be regarded as a moving organ. Generally, the moving organ may be the heart (e.g., cardiac cycle) and/or the lung (e.g., breathing cycle). Also bowel movements may be included; however, alternating movement cycles may be characterized by state-dimensions, such as the breathing cycle or the cardiac cycle. The number of state-dimensions may be one or two, but may also be three or higher. In the region of the torso, for example, 2D- or 3D-images may be combined with at least one state-dimension for the state of the breathing cycle and/or the cardiac cycle.

The coordinates of the state dimensions in the dataset may be realized by a curve of a recorded pilot tone signal. The coordinates are then points on this curve or values of bins of a time interval of this curve. This curve may be a separated part of a measured pilot tone signal. However, the coordinates may also be defined as time delays to characterizing part of a curve (e.g., a heartbeat-curve) or as parts of a curve (e.g., for pattern matching). In one embodiment, in the case of an alternating movement, the coordinates may be defined as values of phases or percentages of one period. For example, the cardiac cycle or the breathing cycle is an alternating movement. With a special point on one period of such curve predefined as "beginning", all other points of the period may be reached by running through $2\pi$ of the phase or from 0% to 100% of the period. Thus, the coordinates themselves may be simple values of the phase or the "percentages," and a measured signal may be compared with a model-curve of one period of the curve (e.g., by pattern matching).

In one embodiment, the multidimensional image-dataset is a 5D-dataset including 3D images combined with the state of the cardiac cycle (e.g., 1st state-dimension) and the breathing cycle (e.g., 2nd state-dimension).

5D whole heart acquisitions that provide high-resolution spatial resolution in a cardiac and respiratory motion-resolved manner (see, e.g., Feng, Li, et al. "5D whole-heart sparse MRI." Magnetic resonance in medicine 79.2 (2018): 826-838) have been presented. This technique provides the basic information of how to obtain 5D data in MRI.

Regarding the act of providing measured pilot tone data from a continuous pilot tone signal acquisition, the measured pilot tone data is relating to a response of the patient to a continuous (e.g., constant) pilot tone signal applied to the patient from a source. The pilot tone data may be provided by measuring a pilot tone signal of a patient when the continuous pilot tone signal is applied during, but also beyond, MRI acquisitions. With this pilot tone signal, each acquisition independent from dimensionality, acquisition scheme, or contrast may be linked to a unique fingerprint, which may be later utilized to match the physiological state across different acquisitions. The application of a pilot tone signal is known in the technical field of MRI, where "tone" is not an audible acoustic wave but is a continuous RF-signal applied from a source (e.g., a coil).

The position of applying the continuous pilot tone signal is generally arbitrary, since in an MRI-system, the continuous pilot tone signal may be measured in the whole examination chamber. However, to get optimal results, the continuous pilot tone signal may be applied in the region of the organ that is to be examined or where the intervention is to occur.

If a model-curve is used for the following act of determining a coordinate, a calibration or registration of the measured pilot tone data or separated pilot tone data, in order to match the model curve may be provided. For example, a maximum of a separated heartbeat-curve of measured pilot tone data does not necessarily have to coincide with the maximum of an ECG-curve; however, the points of the curve of the pilot tone data nevertheless are linked to points of the model-curve. In one embodiment, the correlation of the measured pilot tone data with a model-curve used for determining a coordinate of a state-dimension is defined prior the determination of this coordinate.

Regarding the act of determining a coordinate for each state-dimension based on the measured pilot tone data, the measured pilot tone data includes information about the movement state of an organ (e.g., the heart or the lung).

Since the movement states of an organ are coordinates on a state-dimension (see description above), the measured pilot tone signal may define a region on a state dimension and a point of time on the measured pilot tone signal to a discrete coordinate of a state-dimension. In the case there are two or more state-dimensions, the measured pilot tone signal may identify coordinates on both/all state dimensions, since movements may be separated from a single curve (e.g., measured pilot tone signal) due to characteristic behavior (e.g., by fast Fourier transformation or fitting and subtracting predefined curve-shapes). Thus, in a torso, the movements due to the breathing cycle may be separated from movements due to the cardiac cycle and the state of the breathing cycle, and the cardiac cycle may be defined at a given point of time. The coordinate on the state-dimension of the breath and the coordinate on the state-dimension of the heart may thus be identified.

After that, it is easy to select an image of the multidimensional image-dataset based on the number of determined coordinates of each state dimension, since the coordinates are known and the images in the multidimensional image-dataset are combined with individual coordinates.

Thus, the present embodiments may combine image acquisition (e.g., MR image acquisition) with continuous pilot tone signal acquisition, which may provide real-time data on breathing and cardiac cycle without any additional sensors to be attached to the patient. With the used pilot tone signals, each acquisition independent from dimensionality, acquisition scheme, or contrast may be linked to a unique fingerprint, which may be later utilized to match the physiological state across different acquisitions.

A system for creating a roadmap for a medical workflow according to the present embodiments includes the following components. A database including a multidimensional image-dataset is included. The multidimensional image-dataset includes a plurality of images of a predefined organ combined with a number of state-dimensions characterizing the movement state of a moving organ. A data-interface configured for receiving measured pilot tone data from a continuous pilot tone signal acquisition is also included. A determination unit configured to determine a coordinate for each state-dimension based on the measured pilot tone data is included. A selection unit configured to select an image of the multidimensional image-dataset based on the number of coordinates of each state-dimension is also included.

A method for creating a multidimensional image-dataset according to the present embodiments is configured for a method according to the present embodiments and/or for a system according to the present embodiments. The method includes providing a plurality of images of a predefined organ showing the predefined organ at different states of movement of a moving organ. Regarding the predefined organ and the moving organ, it depends on the nature of the predefined organ, whether the predefined organ is also regarded as a moving organ or not. If the predefined organ is the heart, one state-dimension may recognize the heart also as a moving organ. In the case the predefined organ is the liver, it is not necessary to regard the predefined organ as a moving organ. The moving organ may be the heart or the lung. It is possible to monitor one single moving organ; however, two, three, or more moving organs may be monitored where it is advantageous to separate the influence of two or more moving organs on behalf of the state-dimension. The method includes determining, for every image of the predefined organ, the state of moving of the one or more moving organs. This is done to arrange the images of the predefined organ correctly inside a multidimensional image-dataset, since the states of moving are the coordinates of state-dimensions of the multidimensional image-dataset. The method includes storing each image (e.g., picture) in a multidimensional image-dataset, where each image is connected with the determined state of moving (e.g., a coordinate of the multidimensional image-dataset).

In such multidimensional image-dataset, the altering shape of the predefined organ is pictured in form of a plurality of pictures for many possible movement states of the one or more moving organs.

A multidimensional image-dataset according to the present embodiments is configured for a method according to the present embodiments and/or for a system according to the present embodiments, and may be manufactured with a method according to the present embodiments. The multidimensional image-dataset includes a plurality of images of a predefined organ showing the organ at different states of movement of one or more moving organs, where each picture is connected with a discrete state of moving of the one or more moving organs.

A control device according to the present embodiments for controlling a magnetic resonance imaging system includes a system according to the present embodiments (e.g., at least one of the two systems described above) and/or is configured to perform a method according to the present embodiments (e.g., at least one of the two methods described above). The control device may include additional units or devices for controlling components of a magnetic resonance imaging system (e.g., a sequence control unit for measurement sequence control, a memory, a radio-frequency transmission device that generates, amplifies, and transmits RF pulses, a gradient system interface, a radio-frequency reception device to acquire magnetic resonance signals, and/or a reconstruction unit to reconstruct magnetic resonance image data).

A magnetic resonance imaging system according to the present embodiments includes a control device according to the present embodiments or is at least configured to perform a method according to the present embodiments (e.g., at least one of the two methods described above).

Some units or modules of the system or the control device mentioned above may be completely or partially realized as software modules running on a processor of a system or a control device. A realization largely in the form of software modules may have the advantage that applications already installed on an existing system may be updated, with relatively little effort, to install and run these units of the present application. The object of the present embodiments is also achieved by a computer program product with a computer program that is directly loadable into the memory of a device of a system or a control device of a magnetic resonance imaging system. The computer program product includes program units to perform the acts of the method of the present embodiments when the program is executed by the control device or the system. In addition to the computer program, such a computer program product may also include further parts such as documentation and/or additional components, and hardware components such as a hardware key (e.g., dongle, etc.) to facilitate access to the software.

A computer readable medium (e.g., a non-transitory computer-readable storage medium) such as a memory stick, a hard-disk, or other transportable or permanently-installed carrier may serve to transport and/or to store the executable parts of the computer program product so that these may be read by a processor unit of a control device, an MPSU, or a system. A processor unit may include one or more microprocessors or their equivalents.

Features of different categories may be combined as appropriate to give further embodiments not described herein.

Regarding one embodiment of a method, parallel to the continuous pilot tone signal acquisition (e.g., at the same time), an image acquisition is performed. This image acquisition may be a magnetic resonance (MR) image acquisition and may be optimized to show a device that is used for a, intervention (e.g., a medical operation with a catheter or an endoscope).

In one embodiment, the measured pilot tone data is used to match an acquired image (e.g., MR image) with a corresponding image of the multidimensional image-dataset. This may be achieved as explained above, in that an image of the predefined organ is chosen from the multidimensional image-dataset that matches the actual movement state of the patient (e.g., cardiac cycle and breathing cycle). The image acquisition may be configured such that a device may be tracked in a patient.

In one embodiment, the coordinates of the MR-image and the chosen image from the multidimensional image-dataset may be registered in order to show the device in the right position relative to the organ.

The measured pilot tone data refers to the measured pilot tone signal in that this data is a digital representation of the measured pilot tone signal or separated sub-signals of the pilot tone signal. Tone may provide that the measured pilot tone signal is a curve (e.g., an envelope curve) and the pilot tone data is a digital representation of that curve.

In this respect, in the field of MRI, for example, the contrasts that are optimal to picture an organ are typically not the contrasts used to picture a device (e.g., a catheter or an endoscope in the body). Thus, the MR-images showing a device during an intervention are typically not suited to show the organ or the region around this device properly. Since MRI usually takes a non-neglectable amount of time, other images showing the organ aligned with pictures showing the device may be presented. This may be achieved with the method according to the present embodiments in that images are taken during an operation showing the respective device parallel to the measurement of a continuous pilot tone signal (e.g., the pilot tone data). As discussed above, the pilot tone data may be used to choose pictures from the multidimensional image-dataset (e.g., that should include images of the very patient the operation is performed with). These images picture or better simulate the respective organ at the correct position and shape despite movements (e.g., of the heart or the lung), since the correct picture is selected for each movement state.

According to one embodiment of the method, the measurement of the pilot tone data is connected with the measurement of the central k-space region of the image acquisition. Alternatively or additionally, in the course of determining a coordinate for each state-dimension, the pilot tone data measured at the central k-space region is used. The information may be limited just for central k-space region, since this makes up most of the image information.

According to one embodiment of the method, intervals of the measured pilot tone signals (e.g., the pilot tone data) respective to a predefined time period are stored in the course of pilot tone signal acquisition. Regarding breathing and cardiac activity, these time periods are typically shorter than the period of the breathing cycle or the cardiac cycle. In one embodiment, the coordinate of each state-dimension may be determined by pattern matching of the stored interval with patterns according to coordinates of the state-dimensions.

According to a method, the measured pilot tone data (e.g., the measured pilot tone signal) is analyzed to determine a time delay of a predefined point of the measured pilot tone data respective to a representative point of movement in order to tag a movement state of an organ. In one embodiment, the minimal distance of the determined time delay is used to match an acquired image with a corresponding image of the multidimensional image-dataset. In another embodiment, the representative physiological cardio state is tagged by time delay ($\Delta tC$) relative to the last pilot tone cardiac signal maximum or minimum, and/or the representative physiological breathing state is tagged by time delay ($\Delta tR$) relative to the last pilot tone breathing signal maximum or minimum. This is especially performed with the acquisition of the central k-space line. If the k-space center is acquired multiple times per 2D or 3D image (e.g., spiral out), the average delays may be taken. This option relies on the maxima detection accuracy of the cardiac and breathing PT signal. In one embodiment, two or more time delays (e.g., according to different characterizing points on a curve) are used.

According to one embodiment of the method, for the examination or an intervention regarding a predefined organ, the multidimensional image-dataset includes a plurality of images of this predefined organ in different movement states combined with a number of state-dimensions characterizing the movement state of the heart and/or the lung. The measured pilot tone data represents the cardiac cycle and/or the breathing cycle. An image of the organ is selected from the multidimensional image-dataset that represents the shape of the organ in a movement state based on the determined coordinates. The fingerprint for such 5D acquisition (e.g., if the predefined images are 3D images and both the heart and the lung are monitored) may contain a cohort of many pilot tone signal (e.g., data) pieces or a set of delays per 3D data subset, as already described above. Each subsequent acquisition may include a corresponding fingerprint due to the measured pilot tone signal, which may then be used to match the ideal 3D subset of the multidimensional image-dataset for providing a dynamic roadmap.

Regarding the above embodiment, where samples of the measured pilot tone signal are recorded, for each 3D subset (e.g., image) of the multidimensional image-dataset (e.g., to add to the dataset or to determine the coordinate), the sum of squared differences of the curves of the signal may be calculated for all pilot tone signal pieces of the relevant k-space regions. Specific weighting across the calculated differences between the pilot tone signal pieces may be applied to stress the contribution of the pilot tone signal pieces associated to the central k-space regions. Instead of sum of squared differences between pilot tone signal pieces, correlation metrics may be utilized to determine similarities.

Generally, regarding pattern matching of a recorded pilot tone signal, the multidimensional image-dataset may include reference curves for each coordinate to facilitate a pattern matching.

Regarding the above embodiment, where time delays of the measured pilot tone signal are recorded, the minimal distance of the determined delays ($\Delta tR$, $\Delta tC$) is used to match the acquired image with the corresponding 3D subset of the 5D roadmap data.

Generally, regarding time delays of a recorded pilot tone signal, the multidimensional image-dataset may include time delays for each coordinate to facilitate a matching of time delays.

According to one embodiment of a method, the time difference between two measurements of pilot tone data is determined and used for optimizing the act of determining the coordinates. Each cycle (e.g., the cardiac cycle or the breath cycle) has a defined duration. Depending on the condition of the actual patient, the defined duration may be a little bit faster or slower, but there are typically regions of this cycle that cannot be "reached" in a realistic scenario at least in a short time. Thus, second pilot tone data acquired shortly after first pilot tone data (e.g., which coordinate has been determined) may be localizable at a respective coordinate on the state-dimension (e.g., representing the cycle) after the first coordinate. If the movement cycle was faster or slower, this coordinate may vary a little bit, but not much. Thus, the optimization may be achieved by starting from a coordinate determined on behalf of a first pilot tone data: measuring the time difference to the acquisition of a second pilot tone data; determining a time interval of a curve of the respective motion cycle and/or a coordinate interval of the respective state-dimension that may be reached in the measured time difference (e.g., by involving predefined threshold values for an accelerated and/or decelerated cycle); and determining the new coordinate based on the determined interval. The positive effect of this embodiment is an optimization of calculation time and accuracy, especially if pattern matching is involved.

One embodiment of a system includes a magnetic resonance scanner or a data-interface configured to control a magnetic resonance scanner, where the system may be configured to control an image acquisition of the magnetic resonance scanner parallel to a pilot tone signal acquisition. Additionally or alternatively, a system includes a pilot tone generator or a pilot tone control unit to control a pilot tone generator, where the system may be configured to control a pilot tone signal acquisition parallel to an image acquisition of a magnetic resonance scanner.

One embodiment of a system includes a matching unit configured to match an acquired image with a corresponding image of the multidimensional image-dataset based on the measured pilot tone signal.

The advantages of the present embodiments are the possibility of dynamic roadmap representation from high dimensional datasets either in realtime (e.g., with continuous pilot tone recording and matching) or triggered by arbitrary k-space center readout acquisitions with pilot tone signals. Further, a dynamic roadmap correction of static 3D datasets may be achieved either in realtime by matching a current breathing state from a pilot tone signal to a transversal correction factor.

The present embodiments are compatible with any type of image readout strategy providing a representative respiratory and cardiac pilot tone signal state that does not rely on any specific image contrasts. Further, the method according to the present embodiments is robust against potential image distortions caused by, for example, acquisition strategies, motion artefacts, susceptibility artifacts, etc., and the method is compatible with non-triggered & non-gated acquisitions (e.g., consisting of no other breathing or ECG signals). Instead of selecting the corresponding roadmap, correction deformation fields may be applied to the incoming imaging data based on the deformation difference of the shown 3D roadmap and a currently best matching one. In addition, the present embodiments do not require any additional sensors being attached to the patient, which is of big advantage especially in interventions where many other monitoring devices are required.

DETAILED DESCRIPTION

In the diagrams, like numbers refer to like objects throughout. Objects in the diagrams are not necessarily drawn to scale.

Figure 1:
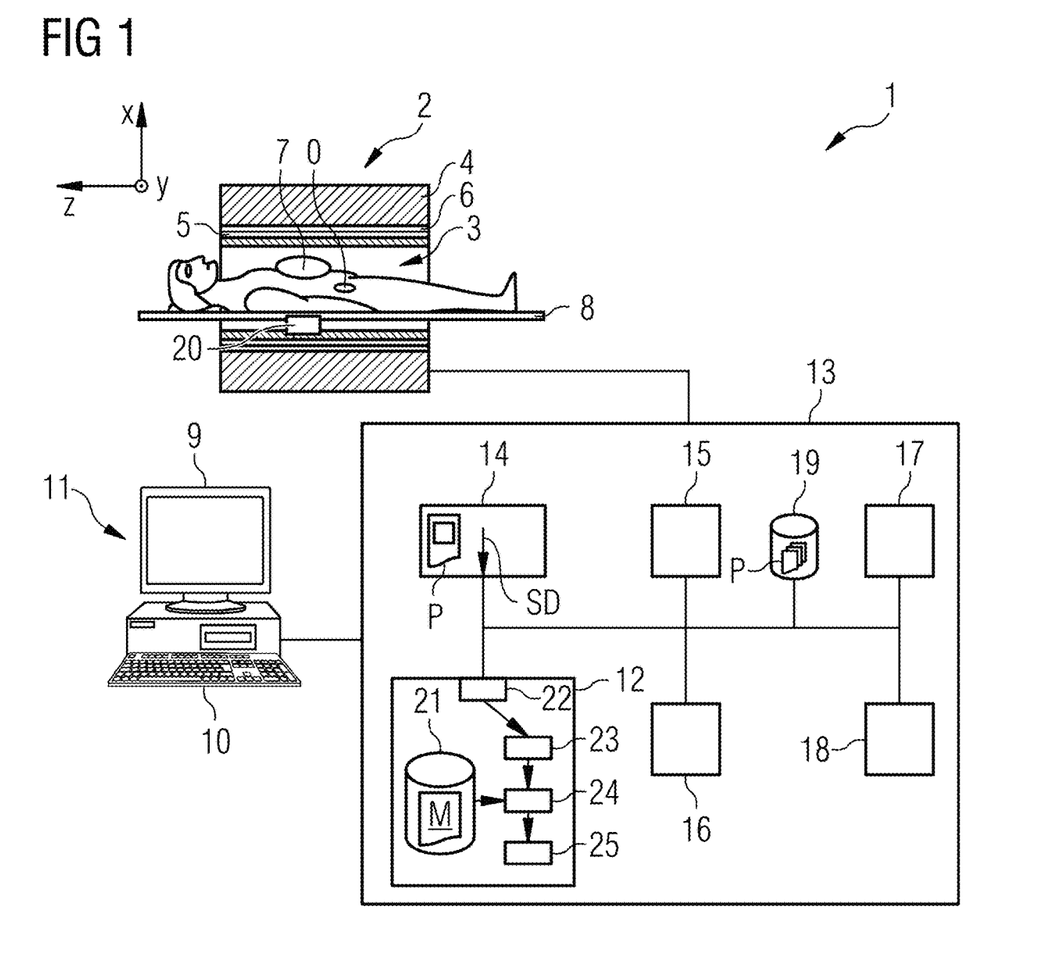
FIG. 1 shows a simplified MRI system with an example for a system according to an embodiment.

FIG. 1 shows a schematic representation of one embodiment of a magnetic resonance imaging system 1 ("MRI-system"). The MRI system 1 includes an actual magnetic resonance scanner 2 with an examination space 3 or patient tunnel in which a patient or test person is positioned on a driven bed 8. An actual examination object is located in a body of the patient.

The magnetic resonance scanner 2 is typically equipped with a basic field magnet system 4, a gradient system 6, as well as an RF transmission antenna system 5, and an RF reception antenna system 7. In the shown exemplary embodiment, the RF transmission antenna system 5 is a whole-body coil permanently installed in the magnetic resonance scanner 2. In contrast to this, the RF reception antenna system 7 is formed as a plurality of local coils to be arranged on the patient or test subject. In principle, however, the whole-body coil may also be used as an RF reception antenna system, and the local coils may respectively be switched into different operating modes.

Figure 4:
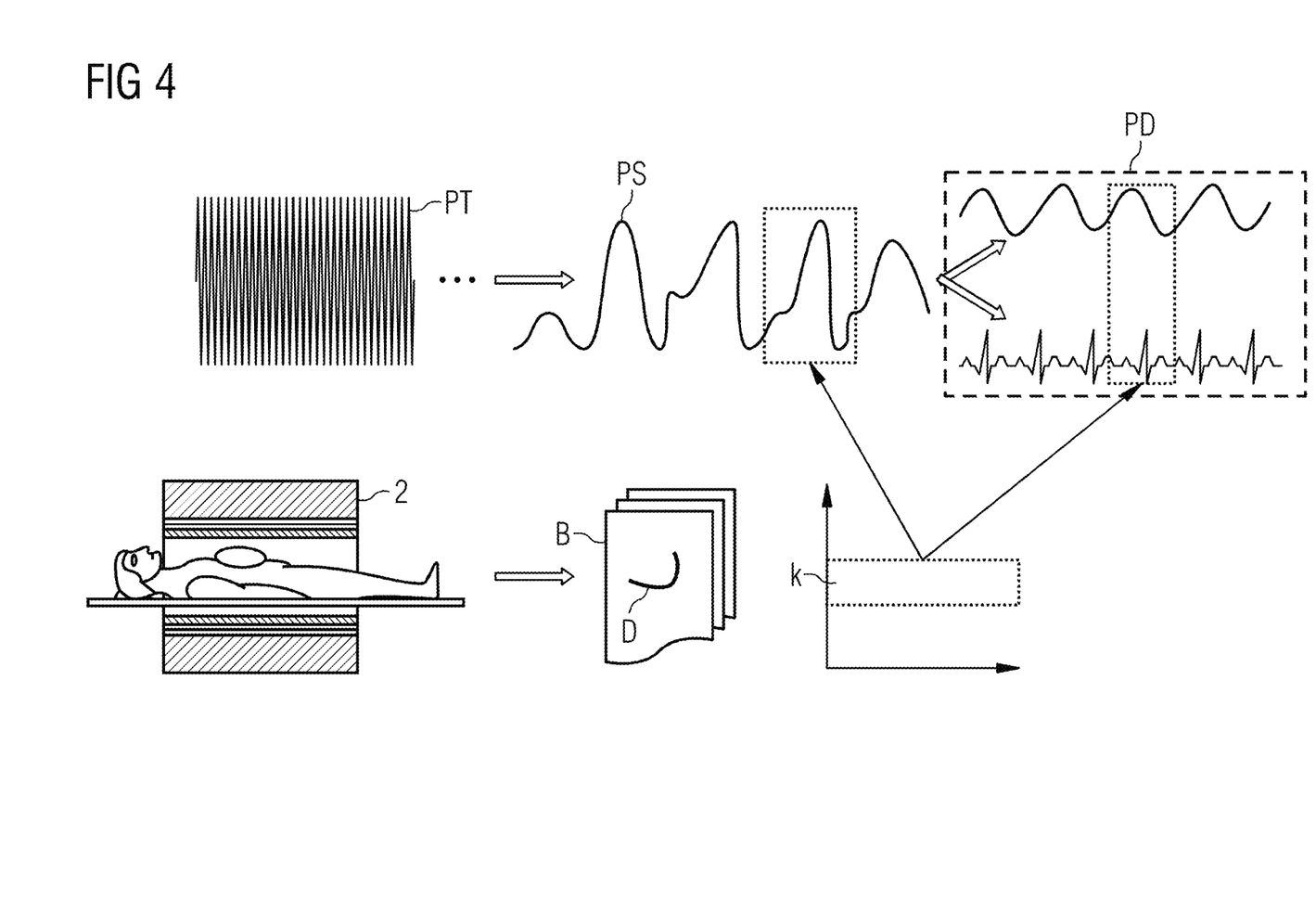
FIG. 4 outlines an example for the acquisition of data.

In this example, the RF reception antenna system 7 is used for measuring the pilot tone signal PS according to the present embodiments (see, e.g., FIG. 4). A generator coil 20 for emitting a continuous pilot tone PT is located below the object O.

The basic field magnet system 4 is configured such that a region of Interest ("RoI") may be recorded. The basic field magnet system 4 is configured in a typical manner so that the basic field magnet system 4 generates a basic magnetic field in a longitudinal direction of the patient (e.g., along a longitudinal axis of the magnetic resonance scanner 2 that proceeds in the z-direction). The gradient system 6 typically includes individually controllable gradient coils in order to be able to switch (e.g., activate) gradients in the x-direction, y-direction, or z-direction independently of one another.

The MRI system 1 shown is FIG. 1 is a whole-body system with a patient tunnel into which a patient may be completely introduced. However, the present embodiments may also be used at other MRI systems (e.g., with a laterally open, C-shaped housing, as well as in smaller magnetic resonance scanners in which only one body part may be positioned).

The MRI system 1 has a central control device 13 that is used to control the MRI system 1. This central control device 13 includes a sequence control unit 14 for measurement sequence control. With this sequence control unit 14, the series of radio-frequency (RF) pulses and gradient pulses may be controlled depending on a selected pulse sequence or, respectively, a series of multiple pulse sequences to acquire magnetic resonance images of the RoI within a measurement session. For example, such a series of pulse sequences may be predetermined within a measurement or control protocol P. Different control protocols P for different measurements or measurement sessions are typically stored in a memory 19 and may be selected by an operator (and possibly modified as necessary) and then be used to implement the measurement.

To output the individual RF pulses of a pulse sequence, the central control device 13 has a radio-frequency transmission device 15 that generates and amplifies the RF pulses and feeds the RF pulses into the RF transmission antenna system 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence.

Moreover, the control device 13 has a radio-frequency reception device 17 (likewise communicating with the sequence control unit 14 in a suitable manner) in order to acquire magnetic resonance signals (e.g., raw data) for the individual measurements, by which magnetic resonance signals are received in a coordinated manner from the RF reception antenna system 7 within the scope of the pulse sequence.

A reconstruction unit 18 receives the acquired raw data and reconstructs magnetic resonance image data therefrom for the measurements. This reconstruction is typically performed based on parameters that may be specified in the respective measurement or control protocol. For example, the image data may then be stored in a memory 19.

Operation of the central control device 13 may take place via a terminal 11 with an input unit 10 and a display unit 9, via which the entire MRI system 1 may thus also be operated by an operator. MR images may also be displayed at the display unit 9, and measurements may be planned and started by the input unit (e.g., possibly in combination with the display unit 9). For example, suitable control protocols may be selected and possibly modified with a suitable series of pulse sequences, as explained above.

The control device 13 includes a system 12 that is configured to perform the method according to the present embodiments. The system 12 includes the following components that may partly appear to be software modules. The system includes a database 21 including a multidimensional image-dataset including a plurality of images A of an organ combined with a number of state-dimensions characterizing the movement state of an organ. As a storage space of the database, also memory 19 could be used. The system also includes a data-interface 22 configured to receive measured pilot tone data from a continuous pilot tone signal acquisition. This data-interface 22 may also be used to receive data of images reconstructed with the reconstruction unit 18. The system includes a determination unit 23 configured to determine a coordinate C1, C2 for each state-dimension D1, D2 (see, e.g., FIG. 3) based on the measured pilot tone signal PS. The system also includes a selection unit 24 configured to select an image $A_{11}$, $A_{12}$, $A_{13}$, $A_{21}$, $A_{22}$, $A_{31}$ of the multidimensional image-dataset M based on the coordinates C1, C2 determined for each state dimension D1, D2. The system includes a matching unit 25 configured to match an acquired image B with a corresponding image $A_{31}$ (see, e.g., FIG. 5) of the multidimensional image-dataset M based on the measured pilot tone signal PS. The acquired image B has been measured with a magnetic resonance scanner 2 parallel to the measurement of the pilot tone signal PS.

The MRI system 1 according to the present embodiments, and, for example, the control device 13, may have a number of additional components that are not shown in detail but are typically present in such systems (e.g., a network interface in order to connect the entire system with a network and be able to exchange raw data and/or image data or, respectively, parameter maps, but also additional data, such as patient-relevant data or control protocols).

Figure 2:
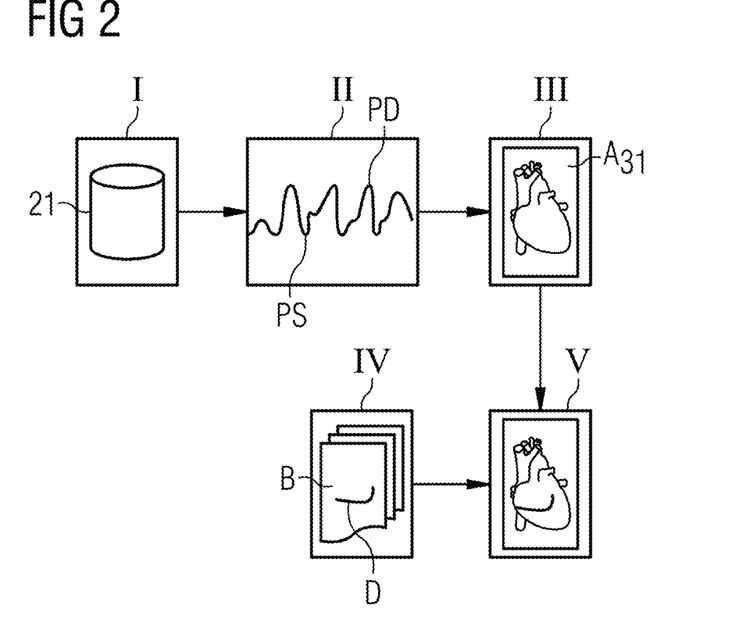
FIG. 2 shows a block diagram of the process flow of a method according to an embodiment.

FIG. 2 shows a block diagram of one embodiment of the process flow of a method according to the present embodiments. A number of acts of the process flow are shown in detail in FIGS. 3 to 5. It is assumed that the method is performed during the examination of a patient.

In act I, a multidimensional image-dataset M is provided (e.g., in a database 21; see, e.g., FIG. 1). The multidimensional image-dataset M including a plurality of images $A_{11}$, $A_{12}$, $A_{13}$, $A_{21}$, $A_{22}$, $A_{31}$ of an organ (e.g., the organ examined) of the patient combined with a number of state-dimensions D1, D2 characterizing the movement state of an organ (e.g., one state-dimension D2 pertains to the moving state of the heart, and one state-dimension D1 pertains to the moving state of the lung).

In act II, measured pilot tone data is provided from a continuous pilot tone signal acquisition. This is done by, for example, measuring a pilot tone signal as a response of the patient to a continuous pilot tone signal applied by a HF-coil.

In act II, a coordinate C1, C2 for each state-dimension D1, D2 is determined based on the measured pilot tone data PD. This act is further explained in FIG. 5.

In act III, an image $A_{31}$ of the multidimensional image-dataset M is selected based on the determined number of coordinates C1, C2 of each state dimension D1, D2.

In act IV, an image acquisition is performed with an MRI system (e.g., as shown in FIG. 1) parallel to the continuous pilot tone signal acquisition. In this example, the image B taken is a 3D picture or a stack of 2D pictures, where the contrasts are chosen such that a device D (e.g., a catheter or an endoscope) may be reconstructed very accurately.

In act 5, the measured pilot tone signal PS is used to match the acquired image B of the device with the corresponding image $A_{31}$ of the multidimensional image-dataset M.

Figure 3:
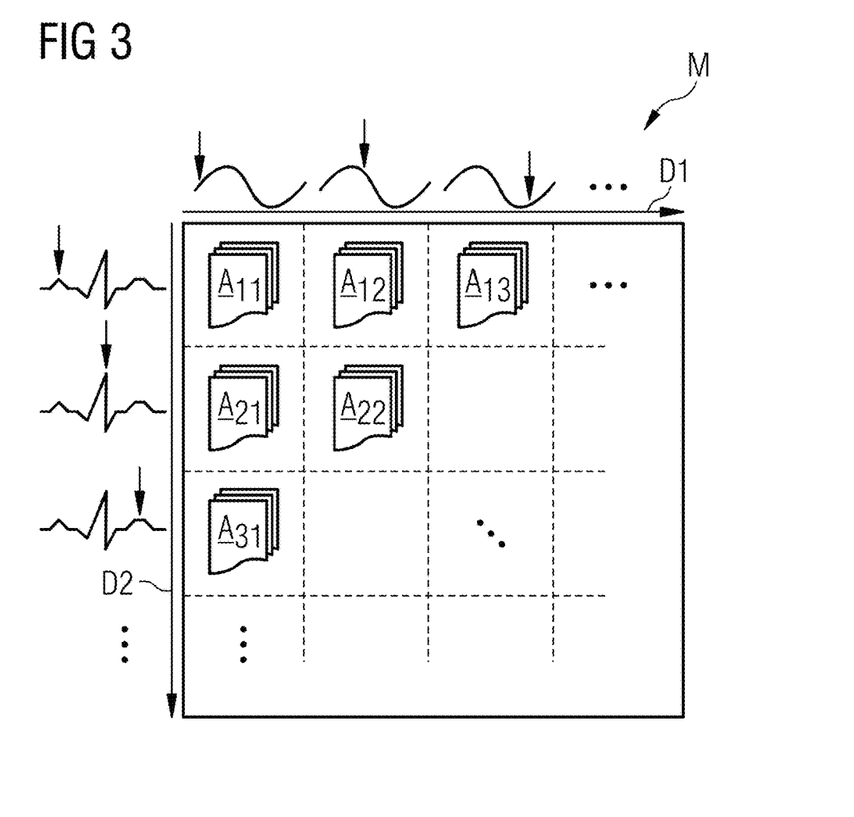
FIG. 3 shows an example of a multidimensional image-dataset.

FIG. 3 shows an example of a multidimensional image-dataset M including a plurality of images $A_{11}$, $A_{12}$, $A_{13}$, $A_{21}$, $A_{22}$, $A_{31}$ of an organ, where these images $A_{11}$, $A_{12}$, $A_{13}$, $A_{21}$, $A_{22}$, $A_{31}$ are combined with two state-dimensions D1, D2. One state dimension D1 characterizes the movement state of the breathing cycle of the lung, and the other state dimension D2 characterizes the movement state of the cardiac cycle. The images $A_{11}$, $A_{12}$, $A_{13}$, $A_{21}$, $A_{22}$, $A_{31}$ show the organ O that should be examined at multiple states during many possible combinations of the moving states of the breathing cycle and the cardiac cycle, where each image $A_{11}$, $A_{12}$, $A_{13}$, $A_{21}$, $A_{22}$, $A_{31}$ is connected with a special coordinate C1, C2 (see FIG. 5) of each state-dimension D1, D2 that fits to the movement state where the image $A_{11}$, $A_{12}$, $A_{13}$, $A_{21}$, $A_{22}$, $A_{31}$ was taken.

For a better understanding, there are pictures showing the breathing cycle at the upper state-dimension D1, where the arrow shows the actual movement state. At the left, the same is shown with the cardiac cycle. Each dashed box inside the solid box (e.g., the multidimensional image-dataset M) should represent one set of 2D-coordinates of the state-dimensions. Each coordinate is connected to a special (3D) image $A_{11}$, $A_{12}$, $A_{13}$, $A_{21}$, $A_{22}$, $A_{31}$ showing the organ at the very special movement state. The more different images $A_{11}$, $A_{12}$, $A_{13}$, $A_{21}$, $A_{22}$, $A_{31}$ for different movement state-combinations the multidimensional image-dataset M includes, the more accurately the roadmap will be.

FIG. 4 outlines an example for the acquisition of data. In the above line of action, a continuous pilot tone signal PT is applied to a patient (e.g., with a frequency of several MHz). This continuous pilot tone signal PT produces as a response in the patient, a pilot tone signal (e.g., an altered pilot tone signal) that may be measured. Behind the upper left arrow, a measured pilot tone signal PS is shown; the curve shown is a curve over the amplitude of the measured pilot one signal PS (e.g., envelope curve). While the applied pilot tone signal has a frequency of about several MHz, the peaks of the measured curve alternate with a frequency of below 1 Hz, where the sampling of this curve is in the region of the applied frequency of the continuous pilot tone signal. In the shown curve of the measured pilot tone signal PS, the breathing cycle and the cardiac cycle are monitored in combination.

To find the coordinates C1, C2 of the state-dimensions D1, D2, the contributions of the breathing cycle and the cardiac cycle may be separated from the measured pilot tone signal PS. This is shown at the upper right, where the data of the separated signals is, for example, the pilot tone data PD. The separation may, for example, be achieved with fast Fourier transformation or by fitting a curve (e.g., for the breathing cycle) and subtracting the fitted curve from the measured pilot tone signal PS (e.g., to get the curve for the cardiac cycle).

In the bottom line of action, an image B (e.g., an actual image) of the patient is taken. The image B is optimized to show a device D (e.g., a catheter) in the patient during an examination or an intervention. Regarding the k-space k of this image B, it is well known that the central k-lines include the most important information for the image. Thus, in this example, the part of the measured pilot tone signal PS that was measured during the recording of the central k-line of the image B is marked (e.g., arrows). The marking is also transferred to the pilot tone data PD.

Figure 5:
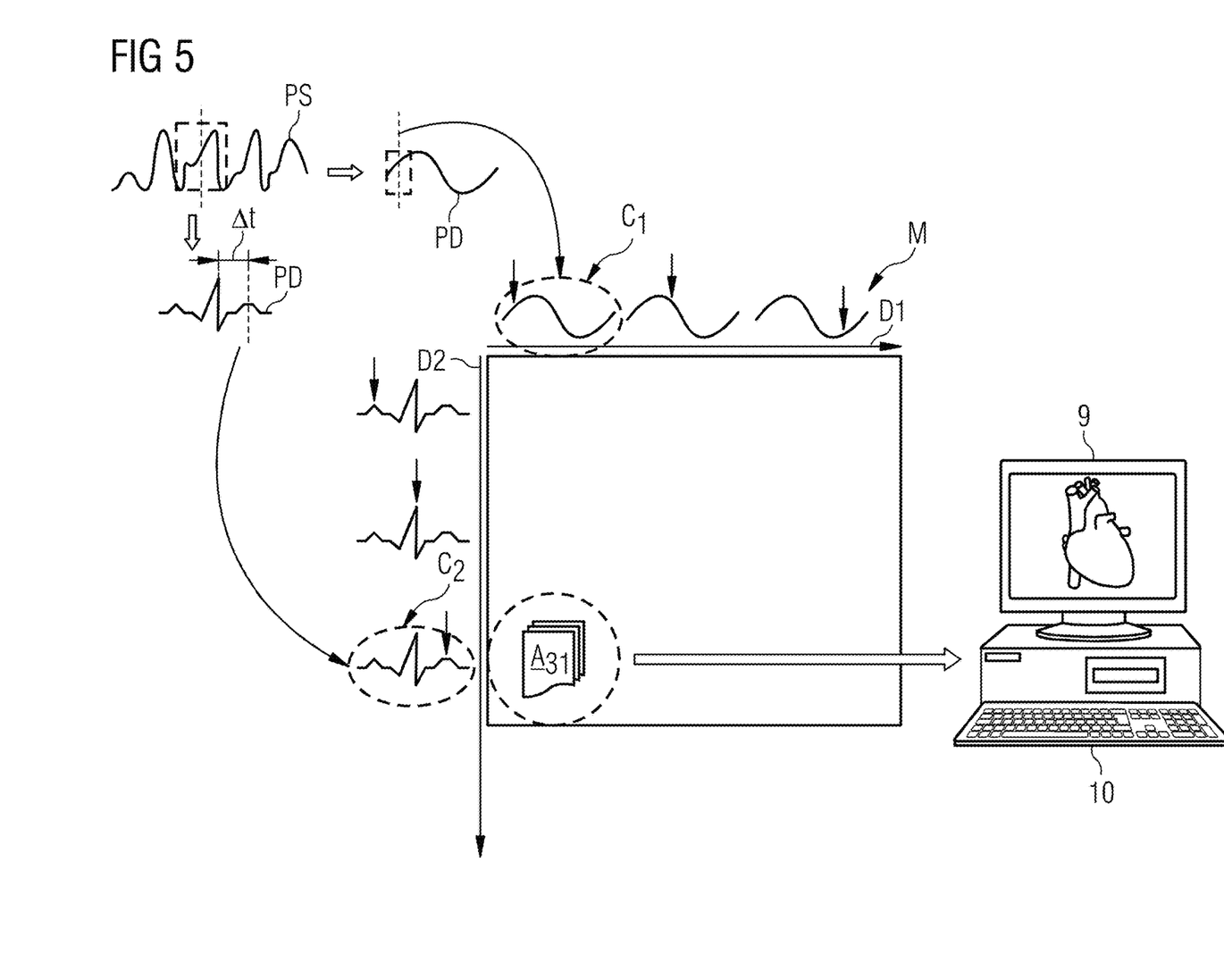
FIG. 5 outlines an example for the determination of coordinates for two state-dimensions and the creation of a roadmap.

FIG. 5 outlines an example for the determination of coordinates C1, C2 for two state-dimensions D1, D2 and the creation of a roadmap. As explained above, the measured pilot tone signal PS is separated into data referring to the breathing cycle and data referring to the cardiac cycle to form the pilot tone data PD. The dashed box shows the time of acquisition of the central k-lines of an MR image B (see, e.g., FIG. 4), where the dotted line marks the center of the dashed box and with that a defined point of time.

Each curve in the pilot tone data is compared with a respective curve of the respective state-dimension D1, D2. The example shows two possible techniques.

The curve pertaining to the breathing cycle is recorded in a time interval around the dotted line. By using pattern matching, the recorded part is compared with parts of reference curves representing the state-dimension (see curves over the upper part of the multidimensional image-dataset M). It is determined that the dotted line is at the position of a definite coordinate C1 of one state-dimension D1 (dashed circle).

The curve pertaining to the cardiac cycle is defined by recording a time distance $\Delta t$ to a characterizing point of the cardiac cycle (e.g., the center of the QRS complex or the R-peak). By comparing this time distance $\Delta t$ with time distances stored with respect to the other state-dimension D2 (see arrows of the curves next to the left part of the multidimensional image-dataset M). It is determined that the dotted line is at the position of a definite coordinate C2 of one state-dimension D2 (dashed circle).

The image $A_{31}$ of the multidimensional image-dataset M is defined with the determined coordinates C1, C2 and chosen for the roadmap. The image $A_{31}$ is shown on the monitor 9 of the computer of the MRI system 1 shown in FIG. 1.

In combination with the present method, especially in the light of FIG. 4, the device D may also be shown now on the monitor 9. Thus, the problem is solved that the organ is usually not optimally visible on the images showing the device D, and with the use of the multidimensional image-dataset M, the organ may be shown in good relation relative to the device D without any errors respective to breathing or heartbeat.

Although the present invention has been disclosed in the form of embodiments and variations thereon, numerous additional modifications and variations may be made thereto without departing from the scope of the invention. For the sake of clarity, the use of "a" or "an" throughout this application does not exclude a plurality, and "comprising" does not exclude other acts or elements. The mention of a "unit" or a "device" does not preclude the use of more than one unit or device.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for creating a roadmap for a medical workflow, the method comprising:
   providing, from a database, a multidimensional image-dataset comprising a plurality of images of a predefined organ combined with coordinates along a number of state-dimensions characterizing a movement state of a moving organ;
   providing measured pilot tone data from a continuous pilot tone signal acquisition;
   determining a coordinate for each state-dimension based on the measured pilot tone data;
   selecting an image of the multidimensional image-dataset based on a number of determined coordinates of each state dimension; and
   performing an image acquisition parallel to the continuous pilot tone signal acquisition,
   wherein the measured pilot tone data is used to match an acquired image with a corresponding predefined image of the multidimensional image-dataset,
   wherein the image acquisition is configured such that the acquired image is taken during an operation to track a device in a patient parallel to the continuous pilot tone signal acquisition, and
   wherein the roadmap is displayed by a display unit to show the device relative to an organ.

2. The method of claim 1, wherein:
   the measurement of the pilot tone data is connected with a measurement of a central k-space region of the image acquisition;
   in the course of determining the coordinate for each state-dimension, the pilot tone data measured at the central k-space region is used; or
   a combination thereof.

3. The method of claim 1, wherein intervals of the measured pilot tone data respective to a predefined time period are stored in the course of pilot tone signal acquisition,
   wherein the coordinate of each state-dimension is determined by pattern matching of the stored interval with patterns according to coordinates of the state-dimensions, and
   wherein the time difference between two acquisitions of pilot tone data is measured and used for optimizing the determination of a coordinate.

4. The method of claim 1, wherein the measured pilot tone data is analyzed to determine a time delay of a predefined point of the measured pilot tone data respective to a representative point of movement in order to tag a movement state of a predefined organ,
   wherein a minimal distance of the determined time delay is used to match an acquired image with a corresponding image of the multidimensional image-dataset, and
   wherein a representative physiological cardio state is tagged by time delay relative to a last pilot tone cardiac signal maximum or minimum, a representative physiological breathing state is tagged by time delay relative to the last pilot tone breathing signal maximum or minimum, or a combination thereof.

5. The method of claim 1, wherein the method is for an examination or an intervention regarding a predefined organ,
   wherein the multidimensional image-dataset comprises a plurality of images of the predefined organ in different movement states combined with a number of state-dimensions characterizing the movement state of a heart, a lung, or the heart and the lung as a moving organ,
   wherein the measured pilot tone data represents a cardiac cycle, a breathing cycle, or the cardiac cycle and the breathing cycle, and
   wherein an image of the predefined organ is selected from the multidimensional image-dataset that represents a shape of the predefined organ in the movement state based on the determined coordinates for each state-dimension.

6. A system for creating a roadmap for a medical workflow, the system comprising:
   a database comprising a multidimensional image-dataset, the multidimensional image-dataset comprising a plurality of images of a predefined organ combined with coordinates along a number of state-dimensions characterizing a movement state of a moving organ;
   a data-interface configured to receive measured pilot tone data from a continuous pilot tone signal acquisition, the continuous pilot tone signal acquisition being parallel to an image acquisition;
   a determination unit configured to determine a coordinate for each state-dimension based on the measured pilot tone data;

a selection unit configured to select an image of the multidimensional image-dataset based on a determined number of coordinates of each state dimension; and
a matching unit configured to match an acquired image with a corresponding image of the multidimensional image-dataset based on the measured pilot tone signal,
wherein the image acquisition is configured such that the acquired image is taken during an operation to track a device in a patient parallel to the continuous pilot tone signal acquisition, and
wherein the roadmap is displayed by a display unit to show the device relative to an organ.

7. The system of claim 6, further comprising:
a magnetic resonance scanner or a data-interface configured to control the magnetic resonance scanner, wherein the system is configured to control an image acquisition of the magnetic resonance scanner parallel to a pilot tone signal acquisition;
a pilot tone generator or a pilot tone control unit configured to control the pilot tone generator, wherein the system is configured to control a pilot tone signal acquisition parallel to an image acquisition of the magnetic resonance scanner; or
a combination thereof.

8. A non-transitory computer-readable storage medium that stores instructions executable by a computer to create a roadmap for a medical workflow, the instructions comprising:
providing a multidimensional image-dataset comprising a plurality of images of a predefined organ combined with coordinates along a number of state-dimensions characterizing a movement state of a moving organ;
providing measured pilot tone data from a continuous pilot tone signal acquisition;
determining a coordinate for each state-dimension based on the measured pilot tone data;
selecting an image of the multidimensional image-dataset based on a number of determined coordinates of each state dimension, and
performing an image acquisition parallel to the continuous pilot tone signal acquisition;
wherein the measured pilot tone data is used to match an acquired image with a corresponding predefined image of the multidimensional image-dataset,
wherein the image acquisition is configured such that the acquired image is taken during an operation to track a device in a patient parallel to the continuous pilot tone signal acquisition, and
wherein the roadmap is displayed by a display unit to show the device relative to an organ.

9. The non-transitory computer-readable storage medium of claim 8, wherein:
the measurement of the pilot tone data is connected with a measurement of a central k-space region of the image acquisition;
in the course of determining the coordinate for each state-dimension, the pilot tone data measured at the central k-space region is used; or
a combination thereof.

10. The non-transitory computer-readable storage medium of claim 8, wherein intervals of the measured pilot tone data respective to a predefined time period are stored in the course of pilot tone signal acquisition,
wherein the coordinate of each state-dimension is determined by pattern matching of the stored interval with patterns according to coordinates of the state-dimensions, and
wherein the time difference between two acquisitions of pilot tone data is measured and used for optimizing the determination of a coordinate.

11. The non-transitory computer-readable storage medium of claim 8, wherein the measured pilot tone data is analyzed to determine a time delay of a predefined point of the measured pilot tone data respective to a representative point of movement in order to tag a movement state of a predefined organ,
wherein a minimal distance of the determined time delay is used to match an acquired image with a corresponding image of the multidimensional image-dataset, and
wherein a representative physiological cardio state is tagged by time delay relative to a last pilot tone cardiac signal maximum or minimum, a representative physiological breathing state is tagged by time delay relative to the last pilot tone breathing signal maximum or minimum, or a combination thereof.

12. The non-transitory computer-readable storage medium of claim 8, wherein the instructions are for an examination or an intervention regarding a predefined organ,
wherein the multidimensional image-dataset comprises a plurality of images of the predefined organ in different movement states combined with a number of state-dimensions characterizing the movement state of a heart, a lung, or the heart and the lung as a moving organ,
wherein the measured pilot tone data represents a cardiac cycle, a breathing cycle, or the cardiac cycle and the breathing cycle, and
wherein an image of the predefined organ is selected from the multidimensional image-dataset that represents a shape of the predefined organ in the movement state based on the determined coordinates for each state-dimension.

* * * * *